(12) United States Patent
Steinberg

(10) Patent No.: US 7,097,625 B2
(45) Date of Patent: *Aug. 29, 2006

(54) SYSTEM AND METHOD FOR NONINVASIVELY EVALUATING A LIMB SUSPECTED OF COMPARTMENT SYNDROME

(75) Inventor: Bruce Steinberg, Jacksonville, FL (US)

(73) Assignee: NCSE, LLC, Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/730,482

(22) Filed: Dec. 8, 2003

(65) Prior Publication Data

US 2004/0116834 A1    Jun. 17, 2004

Related U.S. Application Data

(63) Continuation-in-part of application No. 10/038,040, filed on Oct. 19, 2001, now Pat. No. 6,659,967.

(51) Int. Cl.
*A61B 5/103* (2006.01)
*A61B 5/00* (2006.01)
*A61B 5/03* (2006.01)
*G01N 3/48* (2006.01)

(52) U.S. Cl. ............................ 600/587; 600/561; 73/81

(58) Field of Classification Search ............... 600/488, 600/561, 587, 592, 595; 73/81, 573
See application file for complete search history.

(56) References Cited

U.S. PATENT DOCUMENTS

| 3,680,386 | A |  | 8/1972 | Canon |
| 4,159,640 | A |  | 7/1979 | Leveque et al. |
| 4,739,769 | A |  | 4/1988 | Matthews et al. |
| 4,817,629 | A |  | 4/1989 | Davis et al. |
| 5,038,795 | A |  | 8/1991 | Roush et al. |
| 5,224,469 | A | * | 7/1993 | Mocny ........................ 601/108 |
| 5,564,435 | A | * | 10/1996 | Steinberg .................... 600/561 |
| 5,879,312 | A | * | 3/1999 | Imoto ......................... 600/587 |
| 6,063,044 | A | * | 5/2000 | Leonard et al. ............ 600/587 |
| 6,186,962 | B1 | * | 2/2001 | Lloyd et al. ................ 600/587 |
| 6,659,967 | B1 | * | 12/2003 | Steinberg .................... 600/587 |

FOREIGN PATENT DOCUMENTS

SU           156649          7/1961

OTHER PUBLICATIONS

Horikawa, Ebihoras, Sakai F. Akiyama M.; Non-Invasive Measurement Method for Hardness in Muscular Tissue; Medical & Biological Engineering & Computing—Nov. 1993.

(Continued)

*Primary Examiner*—Charles Marmor
(74) *Attorney, Agent, or Firm*—Holland & Knight LLP

(57) ABSTRACT

A system and method are disclosed for noninvasively diagnosing limb compartment syndrome by measuring a quantitative modulus of hardness. In the preferred embodiment, a nonmovable pressure probe mounted in the center of a movable spring loaded platform is applied against a limb compartment. Force is gradually applied to the probe and the platform, compressing a limb compartment. Pressure on the probe is measured as the probe pushes into the limb. The spring loaded platform displaces, and the distance of the probe tip to the platform is measured. This distance is the depth of compression into the limb by the probe. The relationship of incremental pressures in the probe and the corresponding distance of the probe tip to the platform for each pressure is plotted. A linear regression analysis is preformed whose slope forms a quantitative modulus of hardness.

5 Claims, 9 Drawing Sheets

OTHER PUBLICATIONS

Whiteside, Jr., Thomas E., "Tissue Pressure Measurements as a Determinant of the Need for Fasciotomy", Clin. Orthop., 113:43, 1975.

Steinberg et al., Bruce, "Evaluation of Limb Compartments with Suspected Increased Interstitial Pressure," Clin. Orthop. No. 300, pp. 248-253, 1994.

Horikawa, Ebihoras, Sakai F. Akiyama M., Non-Invasive Measurement Method for Hardness in Muscular Tissue; Medical & Biological Engineering & Computing—Nov. 1993.

Fischer, Andrew "Tissue Compliance Meter for Objective, Quantitative Documentation of Soft Tissue Consistency and Pathology" Arch Phys Rehabil. vol. 68, Feb. 1987, pp. 122-125.

Steinberg, Bruce D. "Evaluation of Limb Compartments with Increased Interstitial Pressure, An Improved Noninvasive Method for Determining Quantitative Hardness" Journal of Biomechanics (2005) 1629-1635.

* cited by examiner

SYSTEM AND METHOD FOR NONINVASIVELY EVALUATING A LIMB SUSPECTED OF COMPARTMENT SYNDROME

CROSS REFERENCES TO RELATED APPLICATIONS

This application is a continuation-in-part of U.S. patent application Ser. No. 10/038,040, filed Oct. 19, 2001, now U.S. Pat. No. 6,659,967, entitled System and Method for Noninvasively Evaluating a Limb Suspected of Compartment Syndrome, the contents of which are incorporated herein by reference.

BACKGROUND OF THE INVENTION

1. Field of the Invention

This invention pertains to the measurement of hardness of the tissue of a limb by using a noninvasive technique. More specifically, the present invention relates to a warning device that safeguards against the development of compartment syndrome by relating hardness to intracompartmental interstitial pressure.

2. Description of the Background Art

The diagnosis of compartment syndrome is made by the direct measurement of intracompartmental interstitial pressure based on a technique developed by Dr. Thomas E. Whitesides, Jr. In this technique, a small amount of fluid is injected into a limb compartment. The pressure necessary to advance the fluid into the compartment is the measurement of the pressure of the compartment. If the intracompartmental interstitial pressure should increase to within 30 mmHg of the diastolic pressure, this could result in irreversible damage of the tissue within the compartment. Treatment for such a condition is emergency surgical release of the fascia overlying the muscle, which is constricting the compartment. Delay in the diagnosis of compartment syndrome and subsequently delay in performing the fasciotomy can result in the needless loss of function, contracture and possible amputation of the limb.

The decision to perform a fasciotomy for a suspected compartment syndrome is frequently difficult. In the classic article by Dr. Thomas E. Whitesides, Jr., "Tissue Pressure Measurements as a Determinant of the Need for Fasciotomy", Clin. Orthop., 113:43, 1975, even if physicians are well versed in the signs and symptoms of compartment syndrome, the clinical analysis sometimes is indefinite and confusing, resulting in delay in performing the fasciotomy.

According to Dr. Whitesides Jr., the one factor that must be present in a compartment syndrome is increased intracompartmental interstitial pressure. Therefore, the effectiveness of the fasciotomy is based on relieving this pressure and re-establishing tissue perfusion. In order to effectively diagnose compartment syndrome, a technique for measuring tissue pressure has been established. For details of the technique of direct intracompartmental interstitial pressure measurement, refer to the article cited above by Dr. Thomas E. Whitesides, Jr.

Compartment syndrome occurs in skeletal muscles enclosed by osseofascial boundaries. The condition develops when accumulating fluid creates high interstitial pressure within a closed osseofascial space, reducing perfusion of surrounding tissues below a level necessary for viability. As the interstitial pressure within the compartment increases, the expansion of the compartment is limited by the compliance of the osseofascial envelope. Like a balloon about to burst, the envelope becomes less and less compliant as the interstitial pressure increases. The change in compliance can be detected by palpation.

Dr. Bruce Steinberg is the inventor of the device described in U.S. Pat. No. 5,564,435. That device quantitatively measures palpation, linear regression of force applied to volume displaced, and has shown a correlation between quantitative modulus of hardness and the interstitial pressure within a compartment. Dr. Steinberg et al. in an article "Evaluation of Limb Compartments with Suspected Increased Interstitial Pressure", Clin. Ortho. No. 300, p 248–253, 1994, demonstrates how such a device can be used to assess compartment pressure with quantitative hardness measurements. Dr. Steinberg, however, has found that this particular device is cumbersome because of its difficulty in application. The device must be applied to a limb with a continuous stable force while a piston mounted within the platform moves to compress the limb. Measurements become inaccurate if there is any movement of the limb or the device. In the setting of a painful limb in trauma, this measurement becomes very difficult because the patient has difficulty maintaining the limb still. The device described by Dr. Steinberg in U.S. Pat. No. 5,564,435 requires that two separate forces be applied simultaneously, the continuous stable force for the force plate and a second force to increase the pressure within the piston. The measurements that derive the hardness result from the piston. As the pressure increases and as the piston compresses the limb compartment, measurements of pressure and displacement are simultaneously recorded while the device is held stable against the limb at a known force plate pressure.

The present invention overcomes this complexity by applying only one force to obtain the measurement of both pressure and displacement. This is done by mounting a stable pressure measuring probe where the piston was previously located. In addition, instead of having the platform as stable and nonmovable, the platform is now spring loaded and moves as pressure is applied to the limb. In effect, the probe pushes against the limb and the platform or force plate moves as the probe forces itself into the limb. The displacement of the probe is now measured by the distance between the probe tip and the movable platform. When removed from the limb, the spring loaded platform realigns to an even level with the probe tip (the spring force is slightly greater than the weight of the platform). In this way, the measurement of pressure within the probe is obtained electronically and the distance between the tip of the probe and the platform is measured as well electronically. A quantitative hardness can be obtained by the relationship between probe pressure and platform displacement. This quantitative measurement of palpation can then be used to assess the interstitial pressure within a compartment. This is a significant improvement over the prior art in that one can now apply a device to the limb with one hand and not worry about the difficulty of maintaining a constant force against the limb with one hand, while then pressurizing the piston mounted within the platform with the other hand. Dr. Steinberg has found with the new device application is faster and easier and the data is significantly more reliable and reproducible.

SUMMARY OF THE INVENTION

It is therefore one of the objectives of this invention to provide a system for noninvasively evaluating a limb suspected of compartment syndrome.

It is also an object of the present invention to evaluate a limb by measuring and recording simultaneous pressure and distance values.

It is a further object of the present invention to make a medical diagnosis on the basis of recorded pressure and distance values.

These and others objects of the present invention are achieved via a noninvasive technique which monitors the condition of limb tissue. More particularly, a noninvasive technique is disclosed for diagnosing and monitoring compartment syndrome. In the preferred embodiment of the invention, a pressure measuring probe is mounted within a spring loaded platform, where the platform is movable and distance is measured relative to the probe. Using this device, one may obtain measurements to assess the hardness of a limb compartment. More particularly, the preferred embodiment of the invention includes an apparatus and method for evaluating the condition of tissue within a limb. The method comprises of the following steps. First applying the apparatus to a limb with a force of application. Second, as this force is increased the change in the pressure of the mounted probe is recorded while the distance that the probe moves into the limb is recorded by the movement of a platform also applied against the limb. The method also includes the step of determining the relationship of multiple points of pressure applied to the probe and travel distance of the probe such that a quantitative hardness curve can be formulated. Additionally, this invention also includes a linear regression analysis of the multiple points of the curve to determine a quantitative hardness modulus.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

The present invention relates to a system and method for noninvasively evaluating a limb for compartment syndrome. The system utilizes a force applicator instrument which is applied to a limb suspected of having the syndrome. The instrument includes a spring biased force plate which is mounted about a probe. This plate is displaced as the instrument is employed in applying an increasing force to the limb. The pressure applied to the probe is detected and recorded, as is the displacement of the force plate relative to the force probe. Linear regression techniques are applied to the pressure and distance data to compute hardness of the limb. A compartment syndrome diagnosis is then made in accordance with the hardness computation. Details of the system and method are elaborated upon more fully hereinafter.

System of the Present Invention

Figure 1:
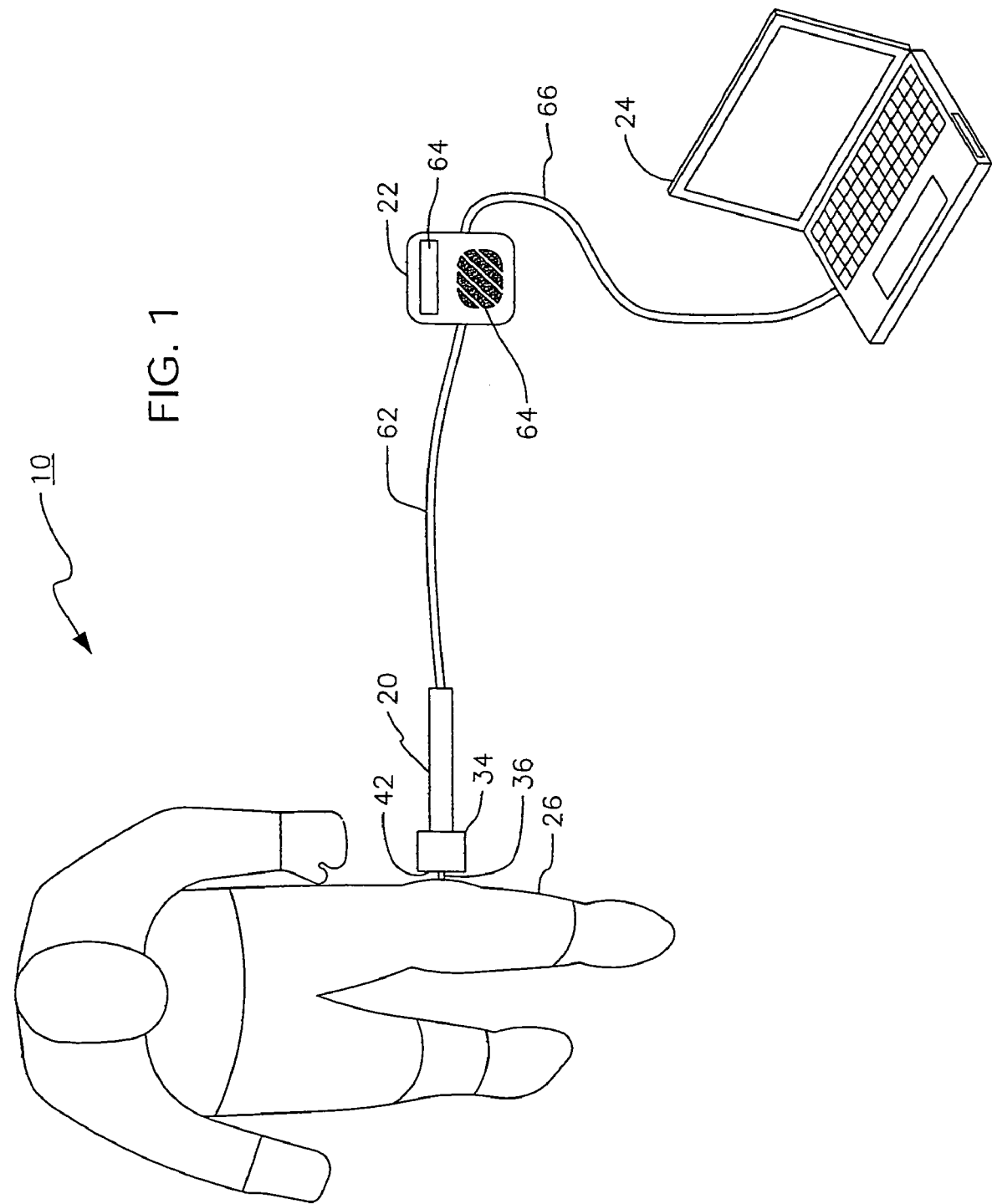
FIG. 1 is a schematic overview of the system of the present invention.
Figure 2:
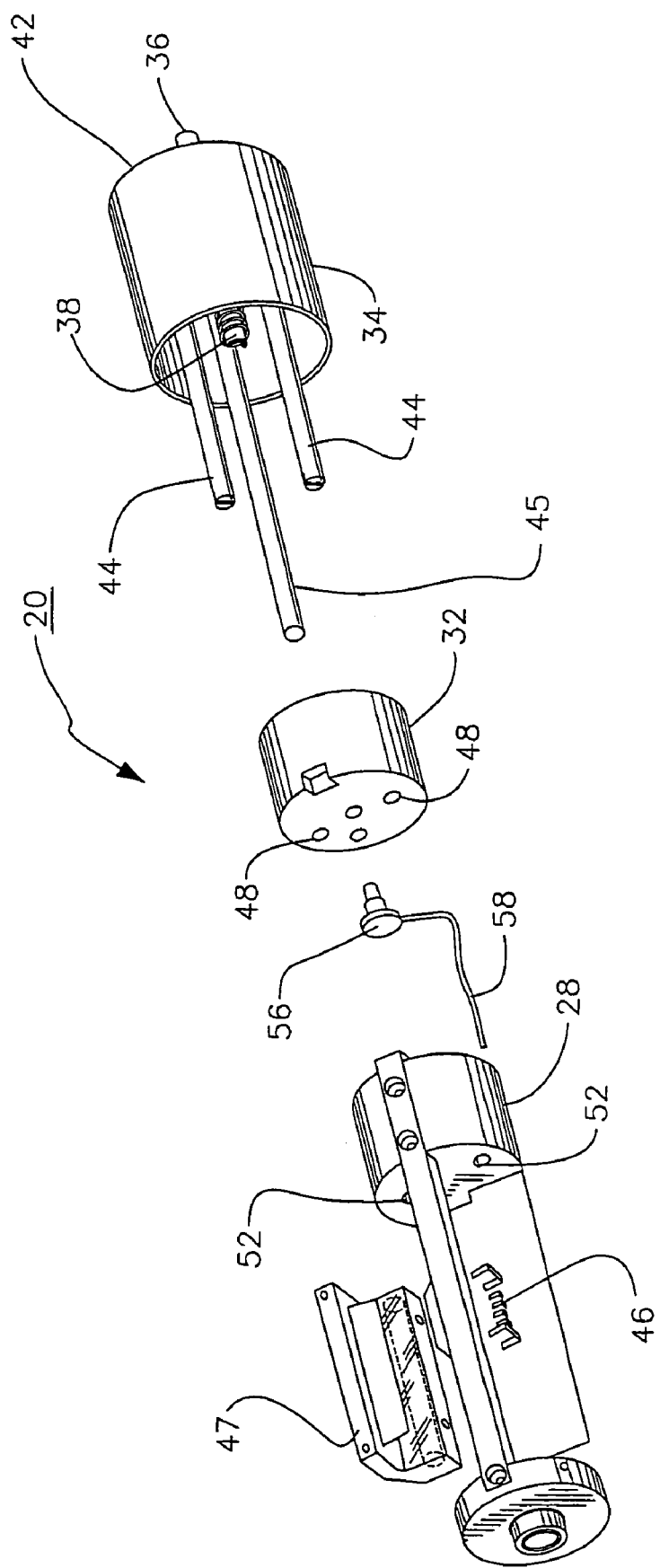
FIG. 2 is an exploded view of the force applicator employed in the system in the present invention.
Figure 3:
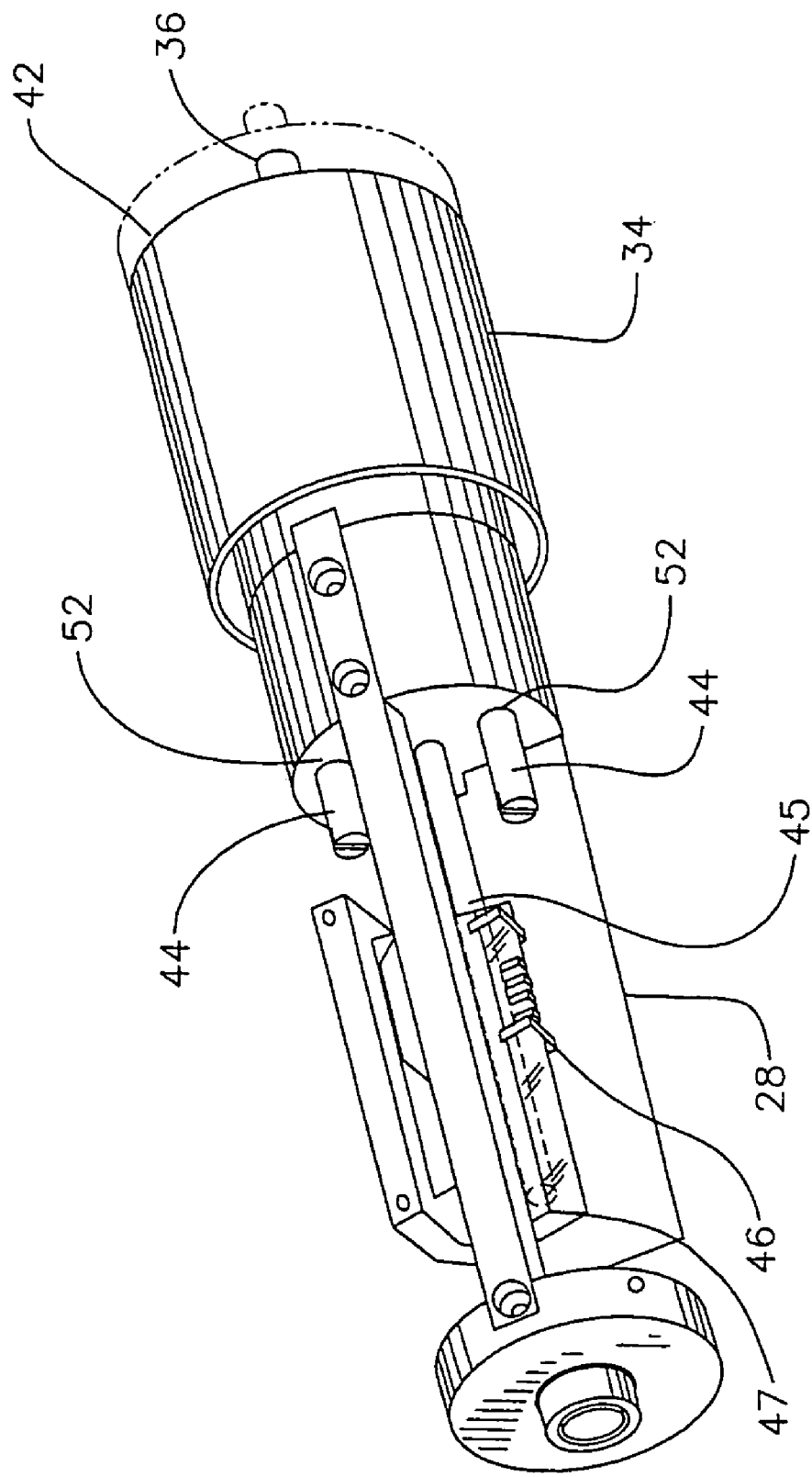
FIG. 3 is an assembled view of the force applicator of the present invention

With reference now to FIG. 1, the system 10 of the present invention is depicted. The system 10 employs an applicator instrument 20, a break out box 22 and a computer 24. Applicator instrument 20 is preferably a hand held device employed by the doctor in applying pressure to a limb 26 of a patient. With reference to FIG. 2, the various components of instrument 20 are depicted in an exploded view. These include: a base portion 28, a housing portion 32, a force plate 34, and a force probe 36. Force probe 36 is preferably positioned through a central aperture within force plate 34. A spring 38 serves to interconnect force probe 36 and force plate 34. More specifically, a helical spring is wound about the end of probe 36 positioned within force plate 34. This connection results in probe 36 and plate 34 being biased with respect to one another. That is, force plate 34 is permitted to slide relative to the probe 36 against the bias of the spring tension. Ideally, the spring tension is selected such that the distal end of probe 36 is flush with the outer face of the force plate 34 with spring 38 in an unbiased state. Thus, prior to the instrument 20 being applied to the limb 26 of a patient, the distal end 42 of instrument 20 presents a relatively flat surface. Thereafter, as the instrument 20 is driven into a limb 26 the force plate 34 is caused to slide rearwardly to expose force probe 36.

With continuing reference to FIG. 2, the stabilizing columns 44 and 45 of force plate 34 are depicted. More specifically, two shorter columns 44 and one elongated column 45 are included. These columns 44 and 45 move linearly within corresponding apertures formed within the housing and base portions (48 and 52, respectively). These columns 44 and 45 are mounted to the interior of force plate 34 and function in guiding the plate 34 as it passes rearwardly over house and base portions (32 and 28, respectively).

Base portion 28 includes an encoder 46 that is employed in measuring the travel distance of elongated stabilizing column 45. Specifically, column 45 is received within apertures formed within housing portion 32, base portion 28, and within an elongated cylindrical aperture formed in L-shaped bracket 47. A portion of bracket 47 is translucent. Encoder 46 includes Light Emitting Diodes (LEDS) that both transmit and detect light. Consequently, light transmitted through the translucent portion of bracket 47 can detect the presence or absence of column 45. In this manner, the position of the end of column 45 within bracket 47 can be detected by encoder 46. This distance measurement corresponds to the travel of force plate 34 relative to force probe 36. This distance measurement is recorded and used in future calculations, as described more fully hereinafter.

A centrally located load cell 56 is interconnected to force probe 36 for use in measuring the pressure applied to force probe 36. This load cell 56 is interconnected to the opposite end of force probe 36 and is positioned intermediate housing portion 32 and base position 28. Specifically, probe 36 extends through the central aperture of housing portion 32 and contacts load cell 56. In the preferred embodiment, probe 36 has a solid, stable and small cross-sectional area relative to the surrounding force plate. A lead 58 is included for passing signals from cell 56 to breakout box 22. As such, pressure applied to probe 36 is transmitted to the load cell 56 where it is measured and recorded. Additionally, force probe 36 and load cell 56 are fixed with respect to the remainder of instrument 20. Consequently, the force applied to instrument 20 by the operator is transferred to both force probe 36 and the limb region 26.

The system thus described is employed in sensing and measuring both pressure and distance values. The pressure values reflect the pressure encountered by force probe 36 as instrument 20 is pressed into a limb 26. The distance measurement reflects the distance between force plate 34 and probe 36 which occurs as instrument 20 is pressed into a limb 26. The components of the system employed in utilizing and analyzing this data are described next.

With reference to FIG. 1 the breakout box 22 of the system 10 is depicted. Box 22 is electrically coupled to applicator instrument 20 by suitable cabling 62. The breakout box 22 functions in receiving pressure measurements from the load cell 56. These values are then compared against preset set minimum and maximum values. When the minimum pressure is met an indicator means 64 within box 22 signals the start of the data sampling period. That is, simultaneous pressure and distance values are recorded for a predetermined length of time only after a threshold pressure value is met. In the preferred embodiment, the threshold pressure value is 25 grams. Reaching this value starts the data acquisition cycle within computer 24, the user is also alerted to the initiation of the cycle by indicator means 64. In the preferred embodiment the sampling time is 3 seconds. Indicator 64 provides audible beeps during the acquisition cycle, preferably one beep per second. Likewise, if the doctor applies too much pressure with instrument 20 the indicator means provides a warning signal. In the preferred embodiment, the maximum pressure is between 7.5–10 lbs. The indicator means 64 can take the form of a audible beep or can be carried out by way of a visual monitor.

Another embodiment of the present invention may include red, yellow and green indicator lights upon the device. This embodiment would tell an examiner if too much force was being applied to the patient. Specifically, the lights would give feedback to an examiner regarding the force rate of application. Due to the viscoelastic nature of the muscle compartment, the faster the rate of application of the indenter against the compartment, the higher the recoded forces and vice versa. For instance, a red indicator light would tell the examiner too much force is being applied too quickly, yellow would indicate too little fore, and a green light would signify the ideal zone for force rate of application. This embodiment would reduce intra-observer variation and make for more consistent readings. This embodiment would also include real time software evaluation of the data and the ability to activate or deactivate the indicator lights.

The computer 24 is also electrically coupled to the breakout box by suitable cabling 66. This computer 24 preferably takes the form of a laptop or desktop computer. However, the computer can also take the form of a specialized data processor specifically adapted for carrying out the present invention. Whatever the form, computer 24 is used in providing electrical power to instrument 20 as well as breakout box 22. Furthermore, computer 24 is employed in collecting, storing, and analyzing the pressure and distance measurements collected by the applicator instrument 20. Once stored within computer 24, the data is analyzed and employed in making diagnostic assessments.

Method of the Present Invention

The inventive method carried out by the system of the present invention is next described. In accordance with the method, the applicator is used by a doctor to apply increasing pressure to a limb region suspected of compartment syndrome. This increasing pressure is applied over a predetermined time period by the distal end of the applicator instrument.

In the next step of the method, the pressure applied to the force probe is repeatedly sensed and measured. These values are then stored over the predetermined time period.

In a similar fashion, the distance between the force plate and force probe at the distal end of the instrument is measured and stored. Again, this measurement is repeatedly taken over the course of a predetermined time period.

The distance and pressure values are then plotted as a curve. An analysis of the curve is then carried out by linear regression techniques to determine a limb hardness. In a final step of the method, a medial diagnosis is made on the basis of the computed hardness.

Handpiece Electronics

The handpiece schematic (FIG. 4) discloses the electronics within the handheld applicator instrument. DC power is supplied by the laptop computer 5 volt bus. A regulated 4.5VDC is created by circuitry E1 (FIG. 4)—a National Semiconductor chip (LM2931CM) to power the load cell. This output voltage powers the force probe load cell FIG. 4, circuitry E3 (Entran Part # ELFM-B1-10L, Fairfield, N.J.) and FIG. 2. When force is applied to the handheld applicator instrument, the force signal from the probe E3 (FIG. 4) is converted to an analog signal in circuit E2 (FIG. 4) and output to connector cable J1 position 2. Within circuitry E2 (FIG. 4) the load cell is wired to J2 and instrumentation amplifier U7 (INA114AU—BurrBrown, Tucson, Ariz.) converts the differential input from the force probe to a calibrated analog output. An output of 10 volts corresponds to the maximum force reading of 10 pounds. This pressure signal goes through connector cable J1 to the breakout box.

Breakout Box Electronics

The breakout box (FIG. 5) performs several functions, as described hereinafter. The box allows an interface from a 50 conductor flat computer cable to a durable small diameter handpiece cable.

Figure 5:
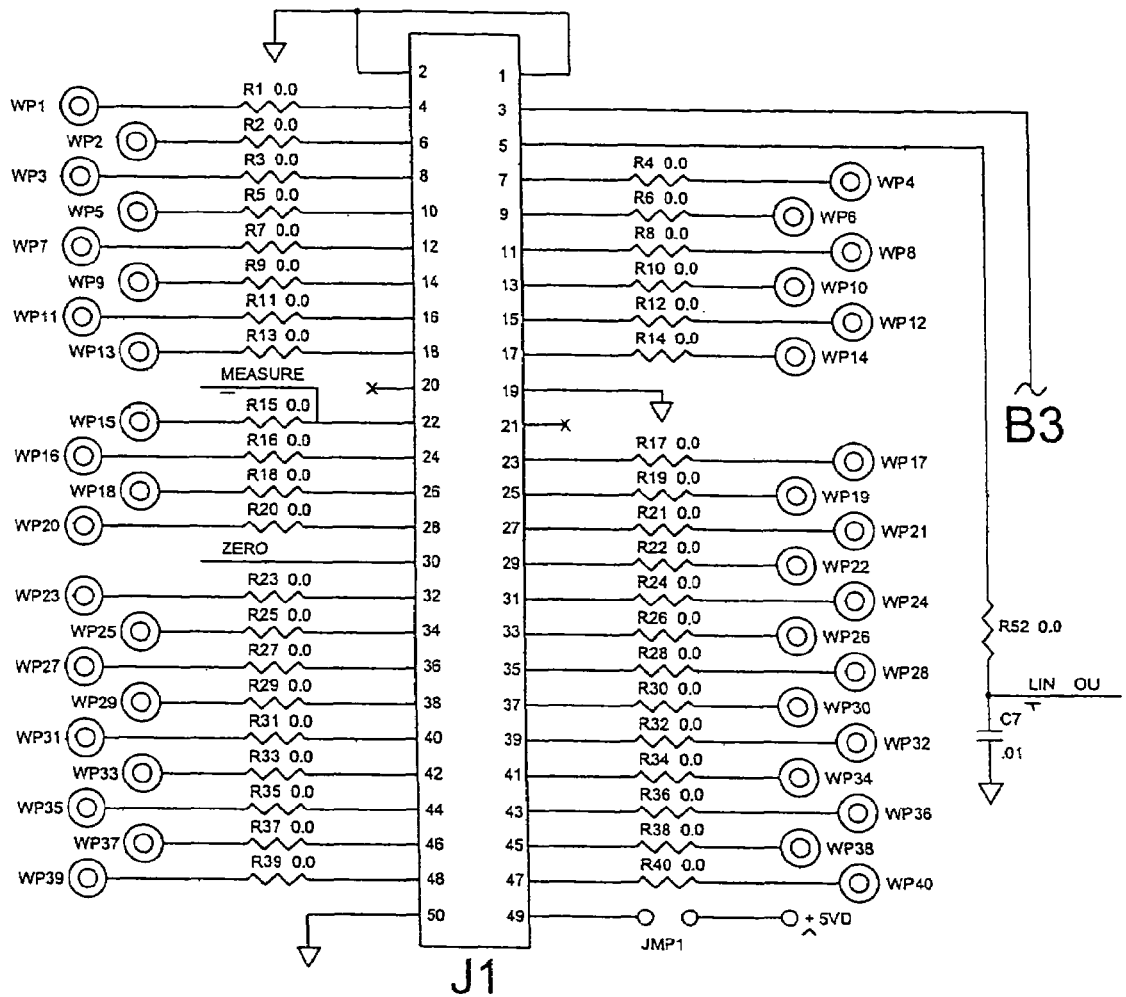
FIG. 5 is an electronic schematic of the breakout box of the system of present invention.
Figure 5:
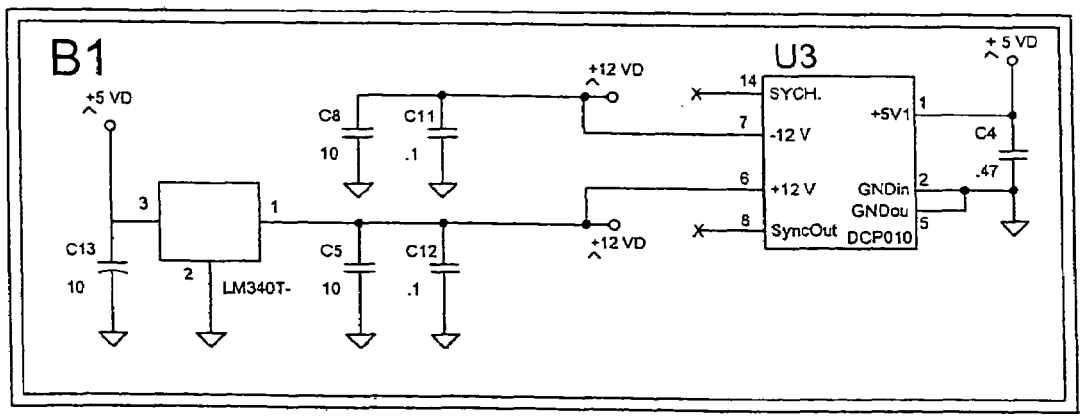
Figure 5A:
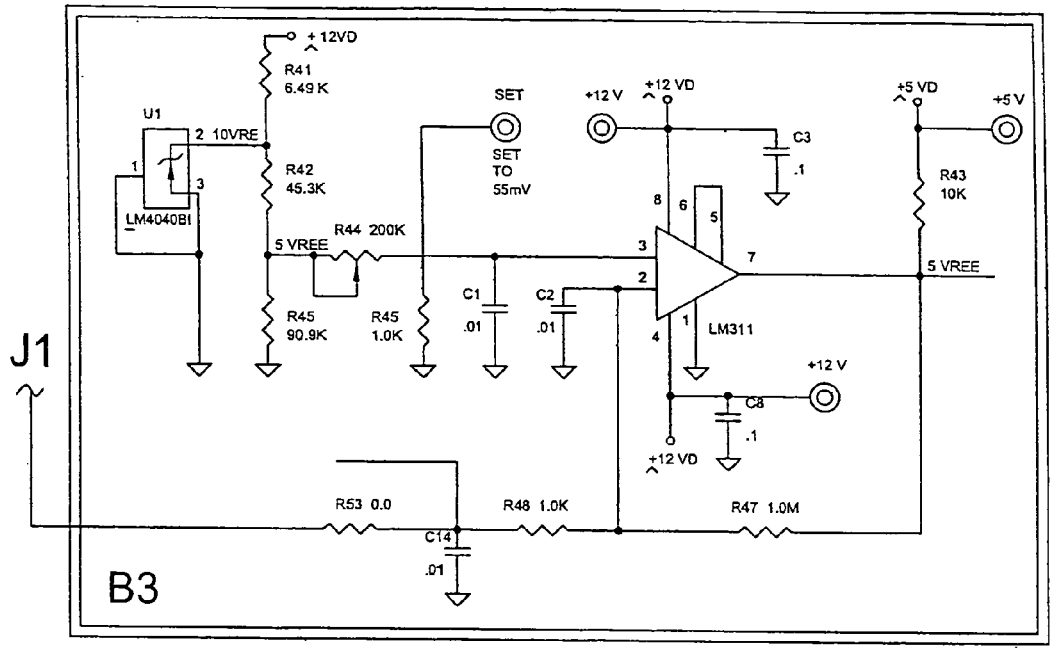
Figure 5A:
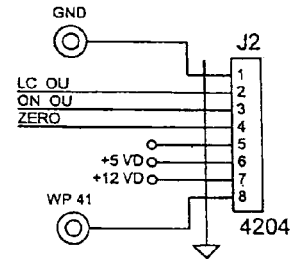
Figure 5A:
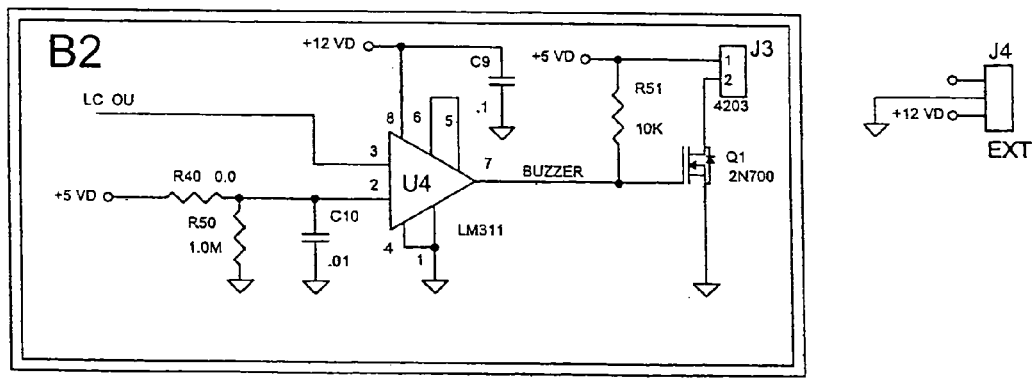

FIG. 5 circuitry B1 also utilizes +5VDC laptop bus and U3 (DCP0105 Burr-Brown Tucson, Ariz.) to create a ±12 VDC supply for analog IC requirements; FIG. 5 circuitry B2 comparator U4 (LM311 National Semiconductor) detects when ten pounds of force is present on load cell, and sounds an alarm to alert the operator (i.e. doctor) that the maximum load cell pressure is being applied.

FIG. 5 circuitry B3 comparator U2 provides a "MEASURE" signal when load cell pressure reaches 25 grams which zeroes the Data Acquisition Card (DAC) in the handpiece and triggers the laptop to begin data acquisition; A 50 conductor flex cable interfaces with the laptop through a data acquisition card (DAQ700) and DAQ software from National Instruments (Lab View).

The displacement of the force plate (FIG. 2) occurs as progressive force is applied to the handheld instrument pushing probe into the limb. Force plate is normally maintained flush with the tip of probe by a spring that maintains a constant force slightly greater than the weight of force plate. (This force is essentially constant regardless of the position of force plate.) This spring (partially shown in FIG. 2) is installed around probe. The force plate has three attached columns that stabilize and direct the displacement of the force plate through the housing of the instrument. As the elongated column (FIG. 2) moves through the housing, optical encoder (USDigital—Vancouver, Wash.) of FIG. 4 circuitry E4 and FIG. 2 generates a series of pulses which are fed to U2, a quadrature decoder interface IC (LS7064 USDigital—Vancouver, Wash.). Signals from U2, (UP/DOWN* directional signal and CLK distance signal) feed into circuitry E5.

Figure 4:
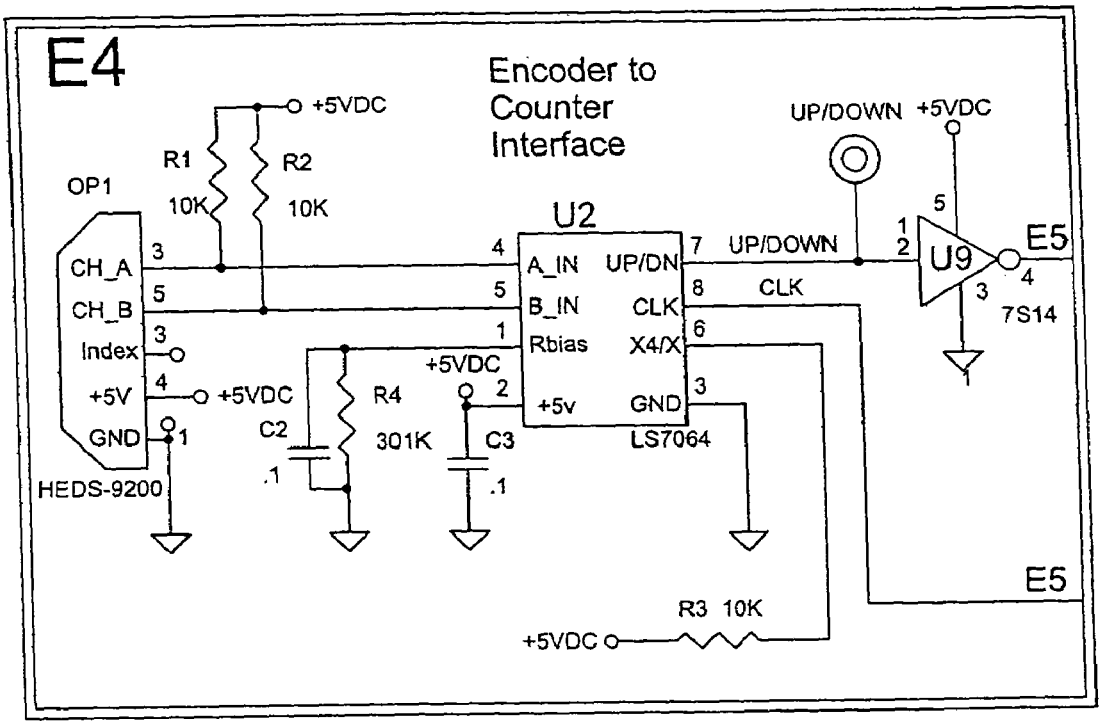
FIG. 4 is an electronic schematic of the force applicator of the present invention.
Figure 4:
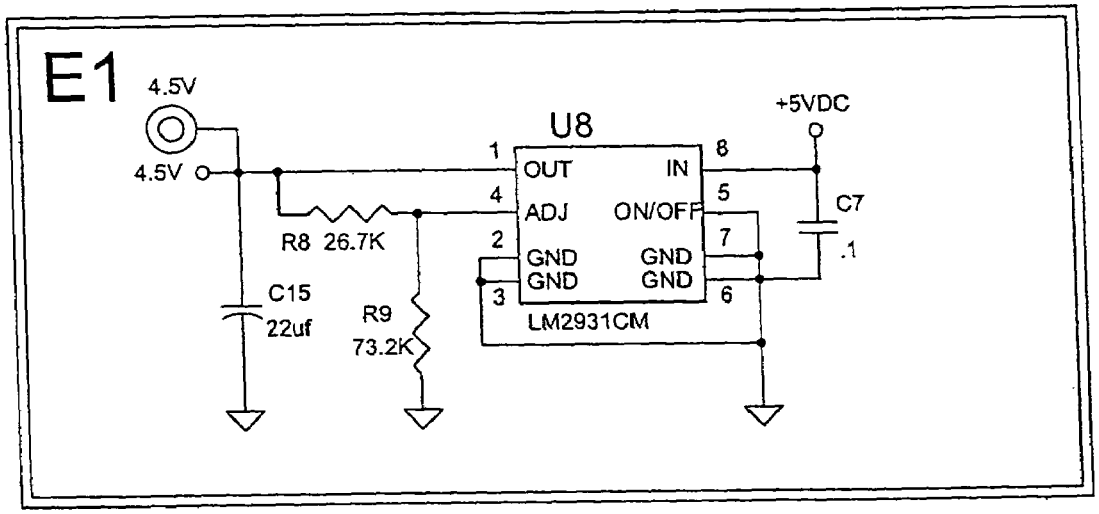
Figure 4A:
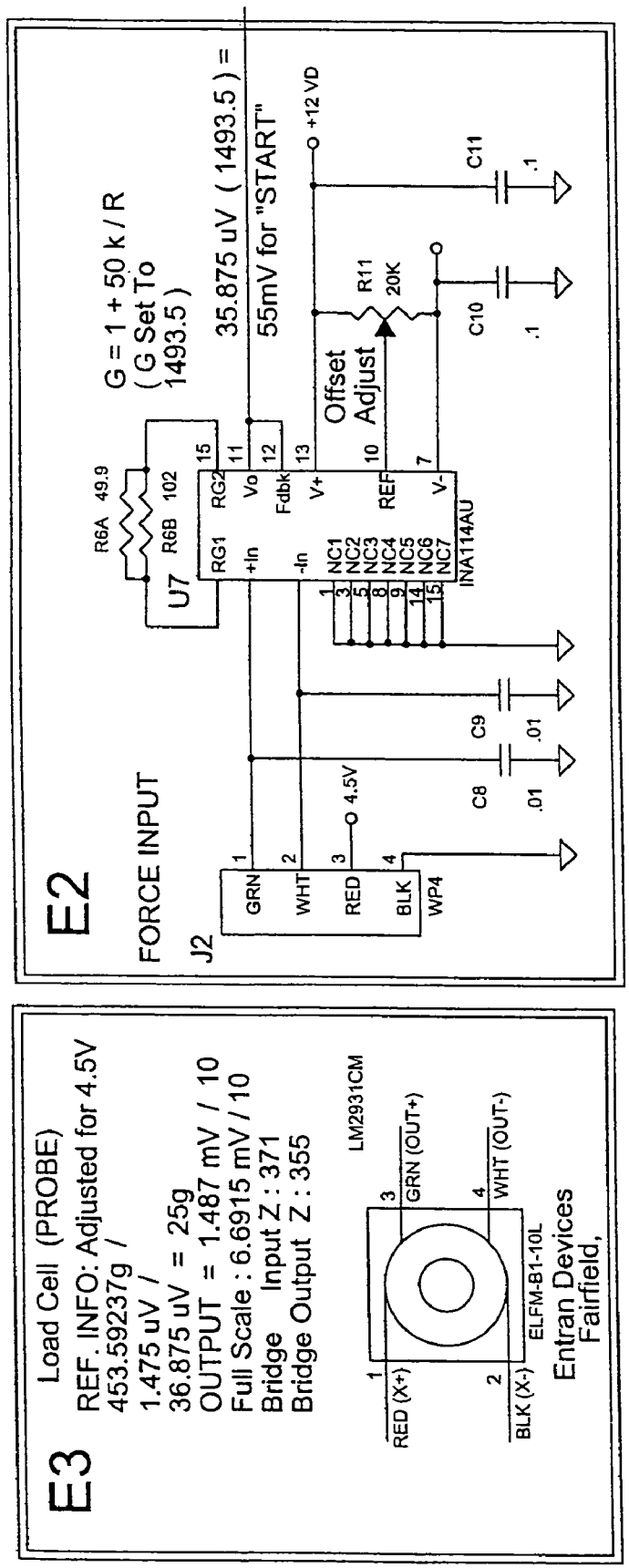
Figure 4B:
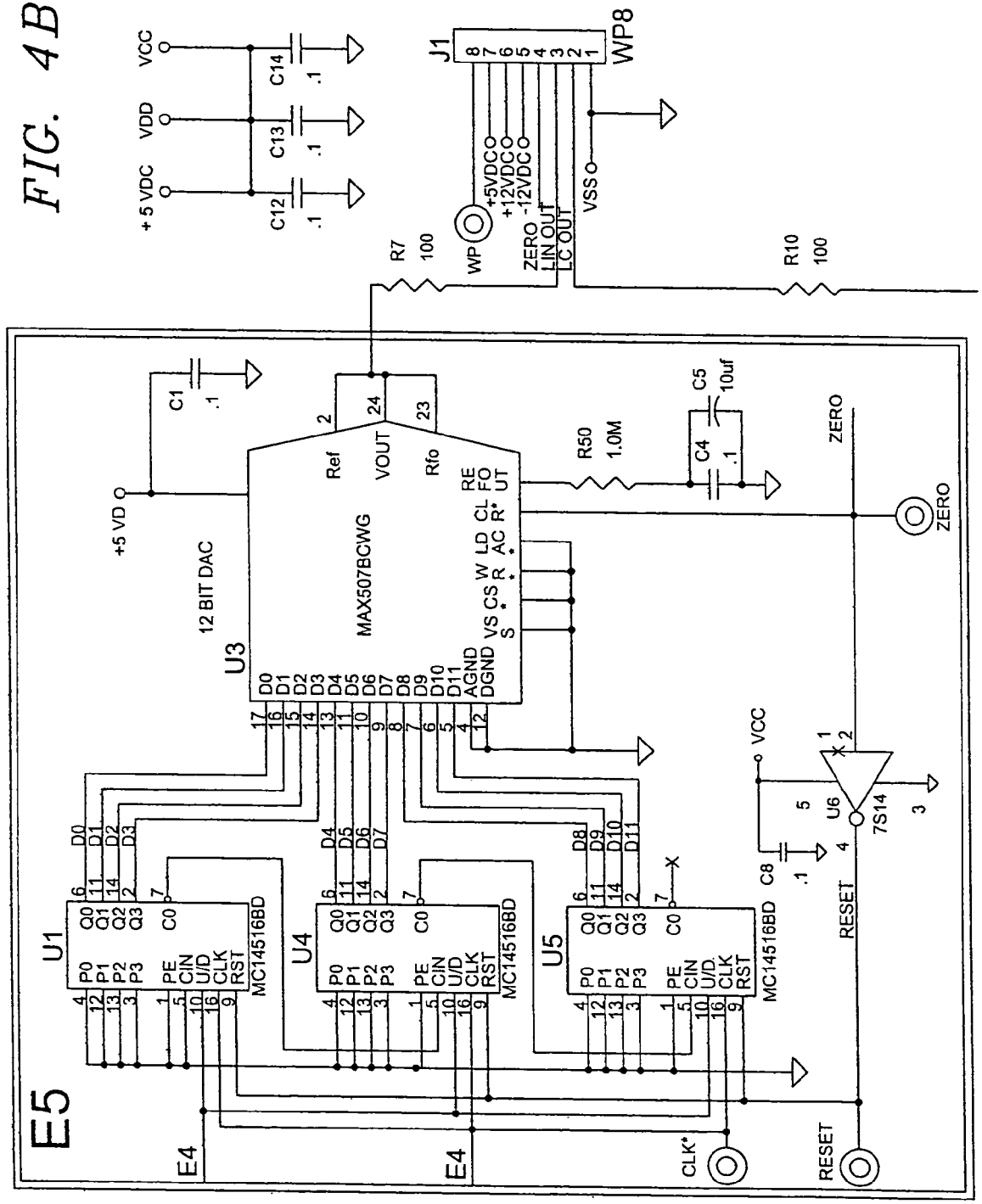

FIG. 4 circuitry E5, a "ripple counter" (12 bit up/down counter) comprised of U1, U4 and U5 increments or decrements based on the input signals from U2. This "displacement" data feeds U3, a 12-bit DAC (MAX507 Maxim Integrated Products—Sunnyvale, Calif.). U3 output signal "LIN_OUT" is then routed to connector cable J1 position 3 and then to the breakout box.

Once initiated, simultaneous pressure and distance measurements are read by the laptop computer data acquisition card (DAC-700 National Instruments—Austin, Tex.) through flex cable L1 from the breakout box.

The laptop performs the following functions: Upon detection of a start signal from circuitry B1 of the breakout box (FIG. 5), begins a three second sample of pressure and distance data; Provides the timing signal for the operator (i.e. doctor) for the duration of the data acquisition phase; Sounds an alarm when 7.5 pounds, and then 10 pounds, of pressure is detected at the load cell.

The software program (LabVIEW National Instruments—Austin, Tex.) plots and displays the points of pressure vs. distance. It also performs a mathematical analysis of the data, including a linear regression analysis based on user selected data ranges. The program is capable of saving the data and repeatedly analyzing the data for replotting and reprinting.

Figure 6:
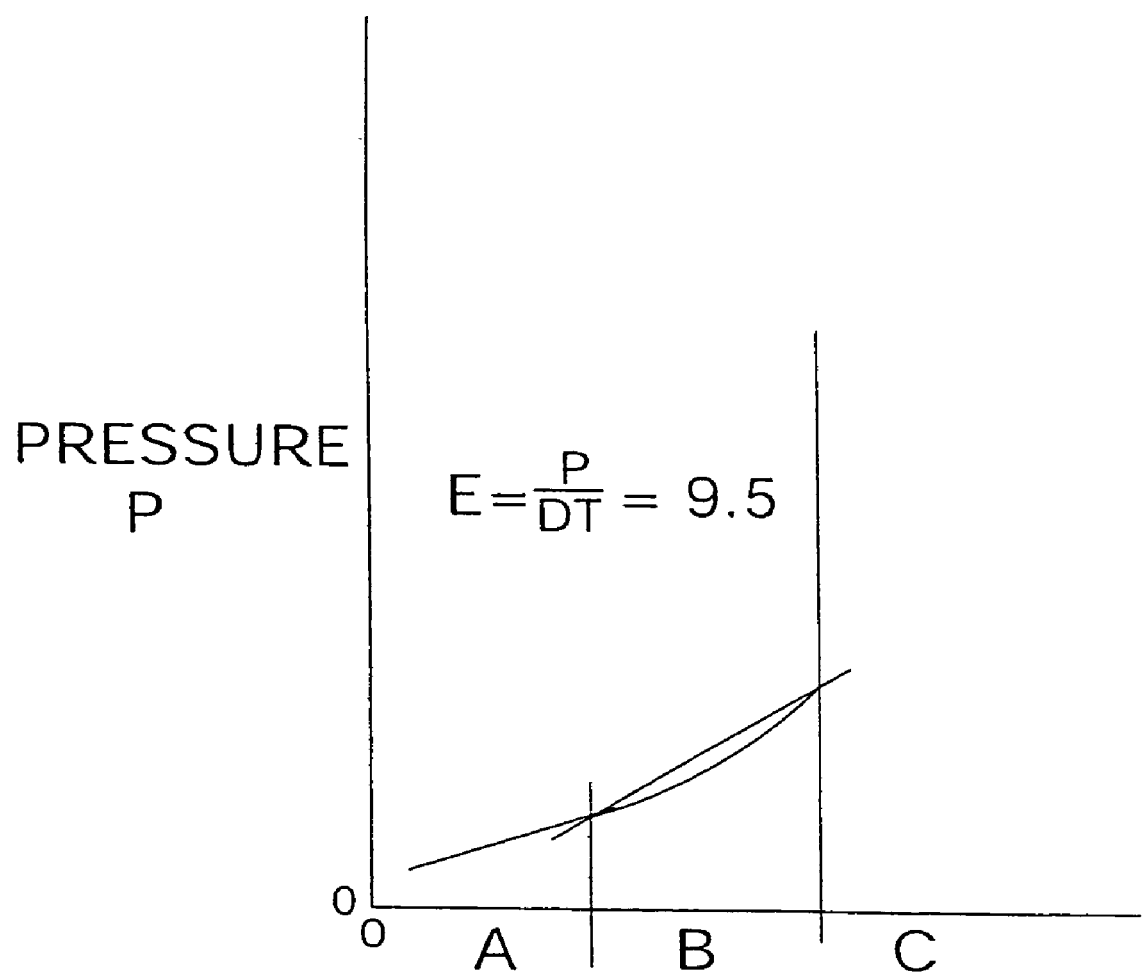
FIG. 6 is chart of displacement vs. pressure as determined by the applicator instrument.

The linear regression of a specific portion of the curve of pressure vs. distance is the hardness measurement of the compartment, note FIG. 6. The plot of the pressure to distance curve has information regarding subcutaneous fat thickness as well as muscle compartment pressure and underlying muscle tone (FIG. 6). These three parts of the curve include the beginning portion (A), mid portion (B) and end portion (C). The initial portion (A) corresponds to the subcutaneous fat portion overlying the compartment. The mid linear portion (B) corresponds to the pressure within the compartment. The end part of the curve (C) is the compaction of the muscle compartment which gives information regarding the tone of the muscle (FIG. 5). The linear regression plot (D) of mid portion (B) gives the hardness value (E) of the muscle.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A device for use in noninvasively evaluating a limb suspected of compartment syndrome, the device comprising in combination:

an applicator instrument including a base portion, a force plate having a cross section, and a force probe, the force probe being positioned through an aperture of the force plate, the force probe having a solid cross section of an area that is substantially smaller than the cross section of the force plate, the force probe and force plate being biased relative to one another, the force plate being permitted to slide relative to the probe, the force plate including at least one stabilizing column which is slidably received within the base portion, an encoder positioned within the base portion for measuring the travel distance of the stabilizing column, such distance corresponding to the movement of the force plate relative to the force probe, a load cell directly connected to the force probe for use in measuring the pressure applied to the force probe, the travel distance and pressure measurements being used to compute modulus of hardness.

2. The device as described in claim 1 wherein the device further includes a series of lights to provide a user feedback regarding the force rate of application of the device.

3. A device for use in evaluating a limb, the device comprising in combination:

an applicator instrument including a force plate and a force probe which are slidably related to one another, the force probe having a solid cross section and being substantially smaller than the force plate, a spring secured about the force probe and biasing the force probe relative to the force plate, an encoder positioned within the instrument for measuring the relative distance between a distal end of the force plate and a distal end of the force probe, a load cell directly interconnected to the force probe for use in measuring the pressure applied to the force probe, wherein the distance and pressure measurements are used in making a medical diagnosis, the travel distance and pressure measurements being used to compute modulus of hardness.

4. The device as described in claim 3 further including a breakout box electrically coupled to the instrument, the breakout box receiving pressure measurements from the load cell, the breakout box including indicator means for signifying the presence of predetermined minimum and maximum pressure measurements.

5. The device as described in claim 4 further including a computer electrically coupled to the breakout box for use in providing electrical power to the instrument and breakout box, the computer being used in collecting, storing and analyzing pressure and distance measurements collected by the instrument.

* * * * *

UNITED STATES PATENT AND TRADEMARK OFFICE
CERTIFICATE OF CORRECTION

PATENT NO. : 7,097,625 B2 Page 1 of 1
APPLICATION NO. : 10/730482
DATED : August 29, 2006
INVENTOR(S) : Bruce Steinberg It is certified that error appears in the above-identified patent and that said Letters Patent is hereby corrected as shown below:

Column 5, line 59 - "yellow would indicate too little fore" should read --yellow would indicate too little force--

Signed and Sealed this

Twenty-eighth Day of November, 2006

JON W. DUDAS
*Director of the United States Patent and Trademark Office*